United States Patent [19]

Insler et al.

[11] Patent Number: 5,588,424
[45] Date of Patent: Dec. 31, 1996

[54] BRONCHIAL BLOCKER ENDOTRACHEAL APPARATUS

[75] Inventors: Steven R. Insler, Cleveland Heights; Erik J. Kraenzler, Brecksville, both of Ohio

[73] Assignee: The Cleveland Clinic Foundation, Cleveland, Ohio

[21] Appl. No.: 495,823

[22] Filed: Jun. 28, 1995

[51] Int. Cl.⁶ .................................................. A61M 16/00
[52] U.S. Cl. .................. 128/207.15; 128/207.14; 128/200.24
[58] Field of Search .................. 128/207.15, 207.14, 128/200.26; 604/99, 101

[56] References Cited

U.S. PATENT DOCUMENTS

| | | | |
|---|---|---|---|
| 3,211,152 | 10/1965 | Stern | 128/207.15 |
| 3,799,173 | 3/1974 | Kamen | 128/207.15 |
| 4,090,518 | 5/1978 | Elam | 128/207.15 |
| 4,233,984 | 11/1980 | Walling | 128/207.14 |
| 4,453,545 | 6/1984 | Inoue et al. | 128/207.15 |
| 4,819,664 | 4/1989 | Nazari | 128/207.15 |

*Primary Examiner*—V. Millin
*Assistant Examiner*—V. Srivastava
*Attorney, Agent, or Firm*—Fay, Sharpe, Beall, Fagan, Minnich & McKee

[57] ABSTRACT

An endotracheal tube (12) ventilates air from the lungs of a patient when inserted into the trachea. A second flexible tube (14) is closely joined to the endotracheal tube (12) in a side-by-side relation. The second flexible tube (14) slidably receives a catheter or endobronchial blocker (16) which has an inflatable cuff (32). The cuff (32) is maneuvered into the right or left bronchus of the patient by sliding and rotating the catheter or bronchial blocker (16) into a position to occlude the selected bronchus. A tracheal cuff (18) is disposed around the endotracheal tube (12) and the second flexible tube (14). When inflated, the tracheal cuff (18) engages the walls of the trachea to reduce passage of air and to secure the position of the endotracheal tube (12).

20 Claims, 4 Drawing Sheets

FIG. IA
PRIOR ART
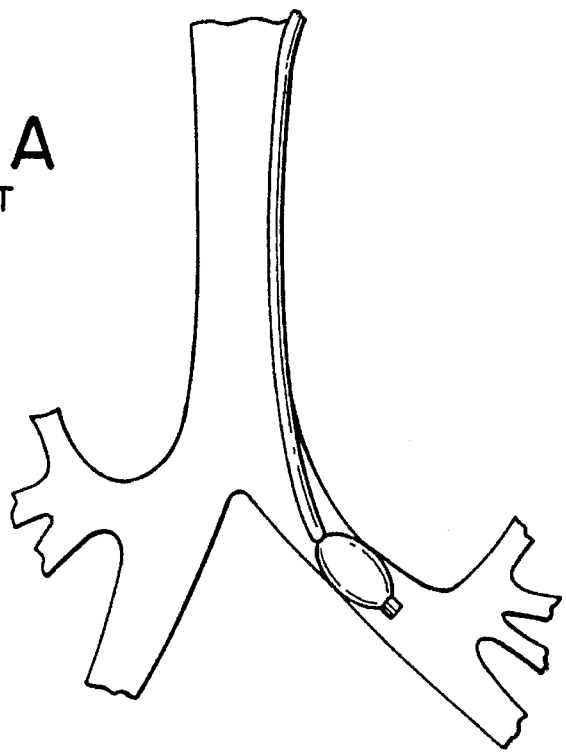
FIG. IB
PRIOR ART
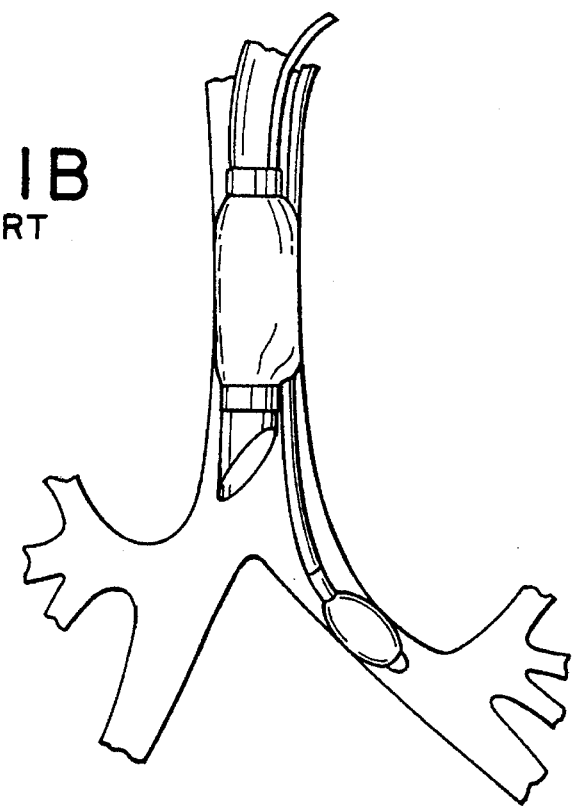

(5,588,424)

BRONCHIAL BLOCKER ENDOTRACHEAL APPARATUS

BACKGROUND OF THE INVENTION

The present invention relates to the one lung anesthesia and ventilation arts. It finds particular application to endotracheal tubes having an endobronchial blocker and will be described with particular reference thereto.

Endobronchial or one lung anesthesia is utilized for a variety of surgical procedures when it is necessary to selectively eliminate ventilation to one portion of the lung. There are a few specific indications for utilizing one lung anesthesia. One is to prevent the spill over of secretions or blood from one area of the lung to other non-involved areas during the perioperative period. The incidence of lung infections requiring surgery, also requires isolation of the infected lung utilizing one lung anesthesia. Lung abscesses poses a major problem with a potential for massive intraoperative spillage and contamination of the contralateral lung. A patient with major hemoptysis requiring pulmonary resection is also a candidate for this technique.

A second indication concerns the need to maintain airway continuity to insure the ability to provide positive pressure ventilation. This occurs in the presence of either an acute or chronic bronchopleural fistula or during operative techniques necessitating interruption of the airway to a lung segment. This typically occurs during a sleeve resection of the bronchus.

A third indication, and perhaps the most common indication for using one lung anesthesia, is the ability to provide better surgical exposure and operating conditions. In addition to the above indications used during surgery, several non-surgical applications have been found. Endobronchial intubation has been used to provide selective positive pressure ventilation during acute respiratory failure. This technique is useful in ICU patients with a large chronic bronchopleural fistula or acute pulmonary disease, especially when associated with major differences in compliance between right and left lungs. Additionally, the technique of bronchopulmonary lavage for alveolar proteinosis, bronchiectasis, and other pulmonary diseases requires the use of endobronchial intubation.

A variety of methods and devices exist to isolate a portion of a lung or an entire lung. Several considerations in choosing the appropriate technique include the nature of the operative procedure, preexisting pulmonary pathology, urgency of the situation, anatomical considerations, and experience of the user.

Intraluminal obstruction of the main bronchi or lobar divisions of the airway has been achieved with the use of several devices, including gauze tampons or specially designed balloon-tip catheters. One device is shown in FIG. 1A and is the Magill balloon-tipped bronchial blocker. This device is a long double-lumen catheter. One lumen is used to inflate a cuff on the distal end of the catheter. The second lumen accommodates a stylet during placement and allows suctioning and degassing of the lung distal to the catheter tip. A bronchoscope, passed with the aid of local or general anesthesia, is used to identify the bronchial segment to be blocked. With the aid of a bronchoscope, the blocker is passed into position and the balloon inflated with sufficient volume to hold the catheter in place. With reference to FIG. 1B, once the catheter is in position, the stylet is removed and a standard cuffed endotracheal tube is placed with the cuff inflated to provide additional stability for the blocker. This device has disadvantages that once the blocker is placed and endotracheal intubation is done, it is difficult to reconfirm the existence of the original position. Slippage of the blocker was common with a change in the patient's position, coughing, or surgical manipulation.

Inoue, U.S. Pat. No. 4,453,545 describes an endotracheal tube with movable endobronchial blocker for one lung anesthesia as shown in FIG. 2. The endotracheal tube has a small channel formed within the wall of the endotracheal tube along most of its length. A balloon-tipped catheter is slidably housed in the small channel and can be extended into the main bronchus. This device has a disadvantage in that the channel formed within the wall of the endotracheal tube impinges upon the inner ventilating diameter of the tube. An additional disadvantage is that the endobronchial blocker is a permanent and fixed portion of the apparatus and is not removable, rotatable, or replaceable.

The present invention provides a new and improved endotracheal apparatus and method which overcomes the above-mentioned problems and others.

SUMMARY OF THE INVENTION

In accordance with the present invention, a new and improved endobronchial blocker method and apparatus for one lung ventilation is provided. A first flexible tube is closely joined in a side-by-side relationship to a second flexible tube. A first inflatable and deflatable cuff extends about both the first and the second flexible tubes toward the distal ends of the tubes. When in use, the first inflatable and deflatable cuff engages the patient's trachea. An endobronchial blocker is slidably received into the second flexible tube. The endobronchial blocker includes an elongated catheter having an inflatable and deflatable cuff disposed about the end of the elongated catheter. The elongated catheter is slidably positioned into the right or left bronchus and the cuff is inflated to occlude the selected bronchus.

In accordance with a more limited aspect of the present invention, an air passage is defined within a wall of either the first or second flexible endotracheal tube and terminates within the first inflatable and deflatable cuff.

In accordance with a more limited aspect of the present invention, the second flexible tube has a diameter which is smaller than the diameter of the first flexible tube.

In accordance with a more limited aspect of the present invention, the first flexible tube and the second flexible tube are joined in contact to each other.

one advantage of the present invention is that it includes two lumens, one lumen for ventilation and the other for accepting an endobronchial blocker.

Another advantage of the present invention is that the endobronchial blocker is independently removable and replaceable without disturbing the fixed position of the endotracheal apparatus during surgery.

Another advantage of the present invention is that since the second flexible tube is a separate tube from the first flexible tube, the ventilating channel of the first flexible tube is unimpinged by the endobronchial blocker. Accordingly, the inside diameter of the first flexible tube used for ventilation is larger and the outside diameter is smaller.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIGS. 1A and 1B show a prior art bronchial blocker;

DETAILED DESCRIPTION OF THE PREFERRED EMBODIMENTS

Figure 3:
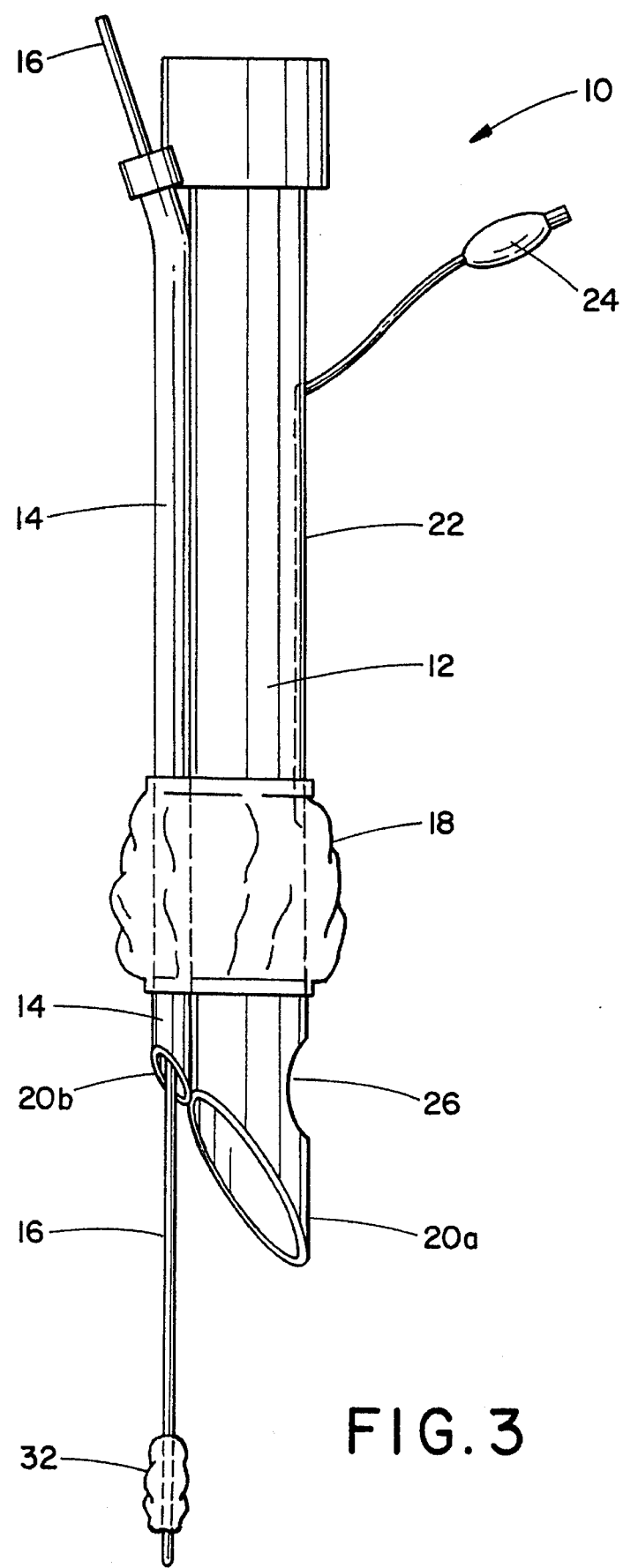
FIG. 3 is an illustration of an endotracheal apparatus in accordance with the present invention; and, FIG. 4 is an illustration of the endotracheal apparatus of FIG. 3 inserted into a patient's trachea.

With reference to FIG. 3, an endotracheal apparatus 10 including a bronchial blocker is shown. An elongated endotracheal tube 12 is preferably molded with about an 8.5 mm inside diameter and about an 11 mm outside diameter when used with an adult patient. The tube 12 is preferably constructed of flexible plastic material such as polyvinyl chloride. It has a sufficient tube length to extend from the patient's mouth to a lower portion of the trachea near the carina when inserted into the trachea. The first flexible tube 12 is a single lumen tube which is adapted to ventilate one or both lungs.

A second flexible tube 14 is closely joined in a side-by-side relationship with the first flexible tube Preferably, the second tube 14 is molded with about a 3.5 mm inside diameter and about a 5.5 mm outside diameter. It has a length substantially equal to the length of the first tube 12. The second tube 14 is adapted to slidably receive instruments to be inserted into the lungs. In the preferred embodiment, the instrument is an endobronchial blocker such as a catheter A low pressure cuff 18 encases and is positioned near to the distal ends 20a and 20b of the concerned tubes. When inserted into the trachea and inflated, the cuff 18 engages the trachea walls restricting the flow of air and securing the position of the tubes 12 and 14. An air passage 22 is defined within the inner wall of the first tube 12 or alternately, in the second flexible tube 14. The air passage 22 communicates air to and from the cuff 18. A cuff inflator 24 contains a valve which is connected to the air passage 22. When activated by manual means such as a syringe, the cuff inflator 24 allows air to be pumped to and from the air passage 22. A valve (not shown) within the cuff inflator 24 regulates the direction of air flow. By releasing the valve, air within the cuff 18 is released to deflate the cuff 18.

In another embodiment, a Murphy's eye 26 is defined near the distal end 20a of the first tube 12. The Murphy's eye 26 is an opening which allows the ventilation of air into the first tube 12 should the ventilating opening at the distal end 20a be blocked. Alternatively, the distal end 20a is angled to reduce the possibility of blockage.

Figure 4:
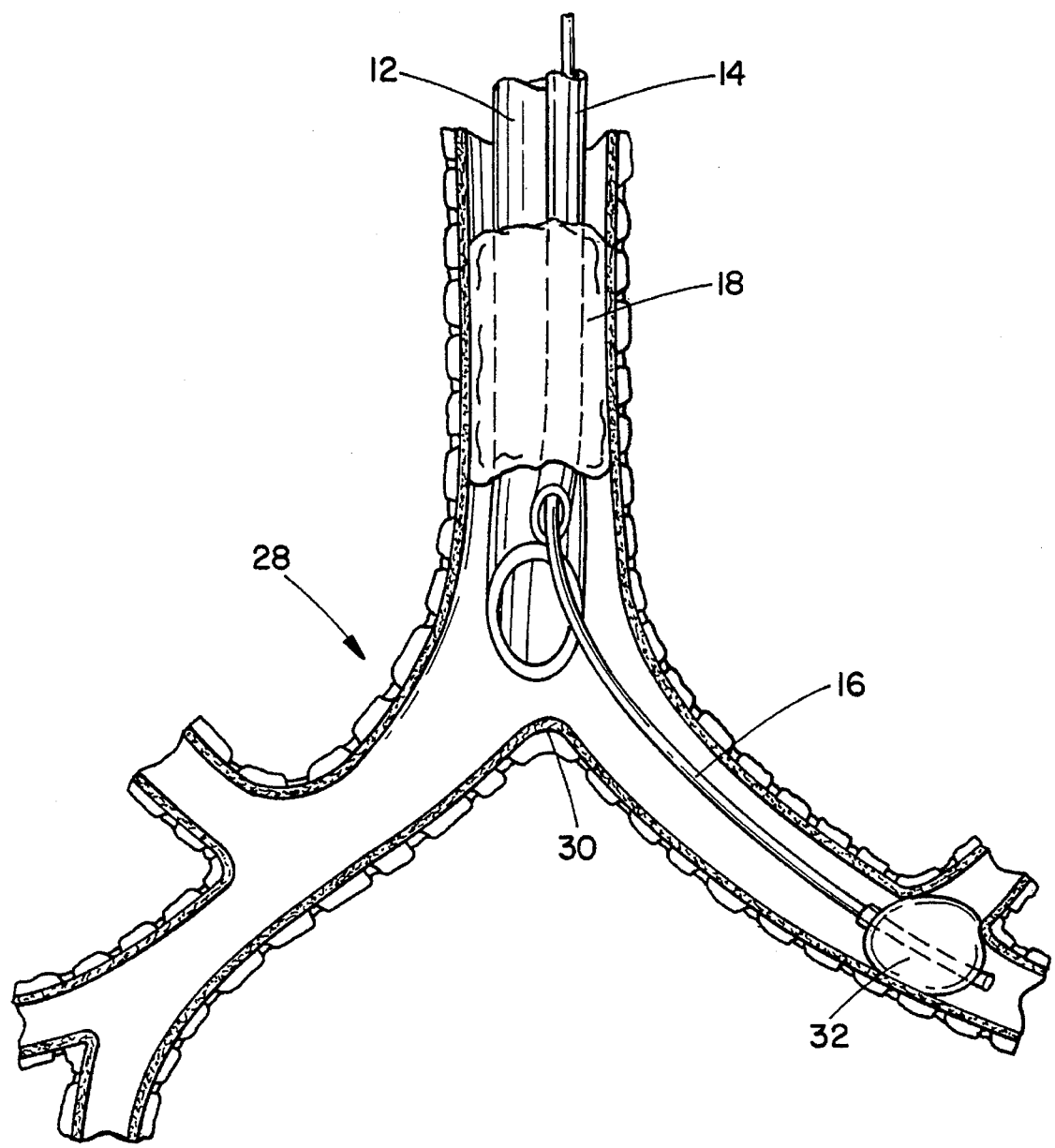
Figure 2:
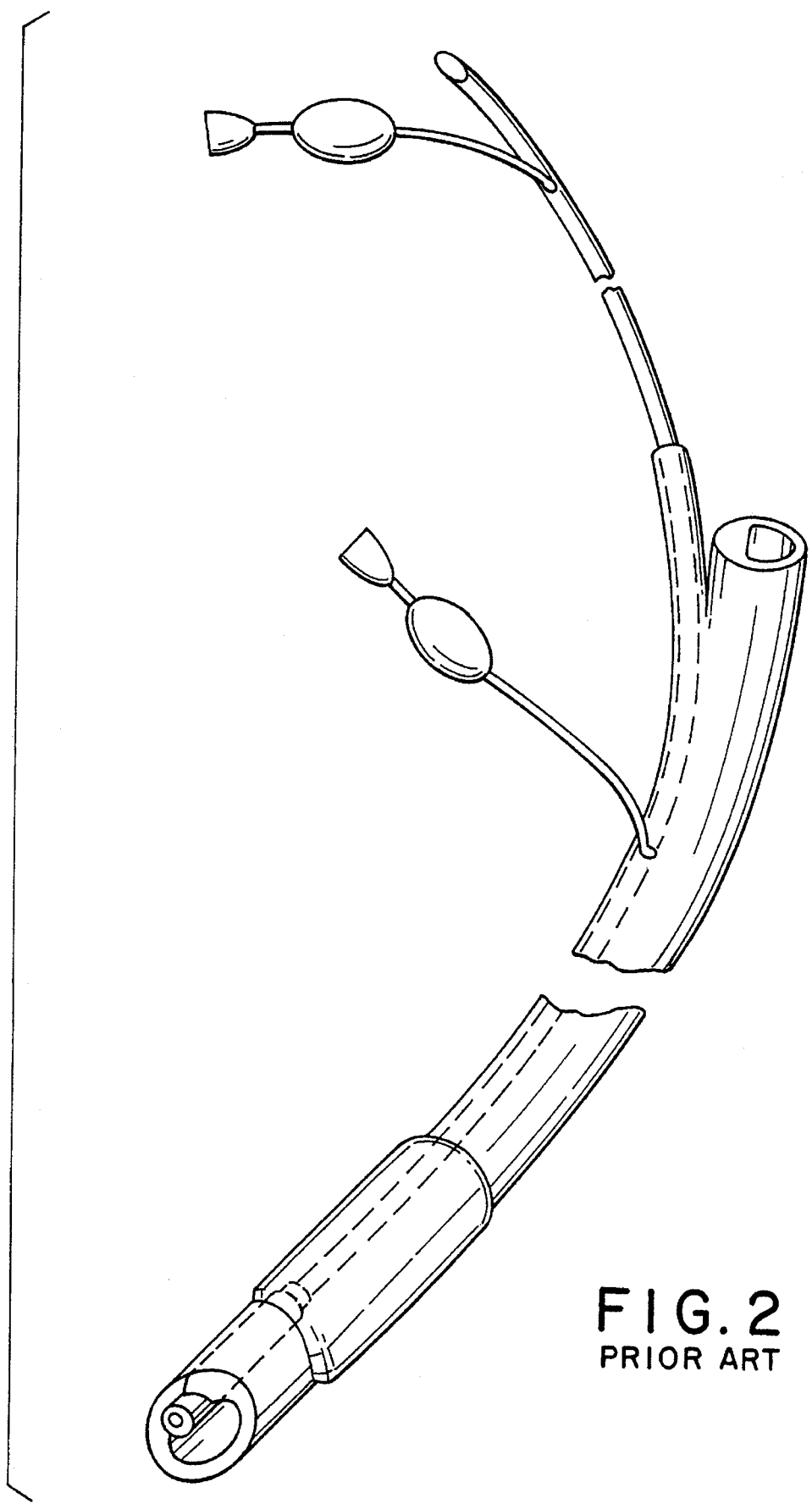
FIG. 2 shows a prior art bronchial blocker.

With reference to FIGS. 3 and 4, during a surgical procedure or for other appropriate needs, the first tube 12 and second tube 14 are inserted through the mouth and into the trachea 28 of a patient with the distal end 20a in place just above the carina 30 of the patient. The proximal end of the tubes 12 and 14 remains accessible from outside the patient's mouth (not shown). The cuff 18 is inflated to engage the trachea walls forming an air seal and fixes the position of the tubes 12 and 14. When in place, the first tube 12 ventilates the lungs.

When it becomes necessary to isolate one of the lungs, an endobronchial blocking catheter 16 is inserted into the second tube 14. The catheter 16 has an inflatable cuff 32 disposed at a distal end. The catheter 16 is slidably maneuvered through the second tube 14 until the catheter 16 extends beyond the distal end 20b of the second tube 14. At that point, the catheter 16 is maneuvered and rotated into the bronchus to be occluded until the inflatable cuff 32 is in a position to occlude the bronchus. To assist in the positioning of the inflatable cuff 32, a fiberoptic bronchoscope (not shown) is inserted through the first tube 12 allowing an operator direct vision within the trachea 28. Once the cuff 32 is in position, the cuff 32 is inflated by an air pump (not shown) communicating with an air passage (not shown) within the catheter 16. When inflated, the cuff 32 occludes the airway of the bronchus to allow for one lung ventilation.

The catheter 16 is fully removable. If the inflatable cuff 32 is ruptured during surgery, the catheter 16 is simply withdrawn through the second tube 14 and replaced without disturbing the fixed position of the first and second tubes 12 and 14.

In the preferred embodiment, the side-by-side relationship of the first tube 12 and the second tube 14 is generally in an axial direction with the outer surface of the second tube 14 directly secured to the outer surface of the tube 12. Alternately, the second tube 14 is secured to the endotracheal tube 12 without being in direct contact such as by using struts or a web. In another embodiment of the invention, the second tube 14 is disposed in a variety of side-by-side relationships to the first tube 12 such as a helical or circular structure.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An endotracheal apparatus for insertion through the mouth and into the trachea of a patient for ventilating one lung and blocking the other lung comprising:

a first elongated flexible tube having an external wall portion, a proximal end and a distal end, the distal end being positioned in the trachea when in use and adapted for ventilating air;

a second elongated flexible tube, separate from the first tube, having a proximal end and a distal end, an external wall portion of the second elongated flexible tube being closely joined in a side-by-side relation to said external wall portion of the first elongated flexible tube, the second elongated flexible tube for receiving an endobrochial blocker;

a first inflatable and deflatable cuff extending about the first and second elongated flexible tubes toward the distal ends of the first and second tubes, the first inflatable and deflatable cuff being positioned and operable when inflated to engage the trachea;

an endobronchial blocker comprising an elongated catheter having a proximal end and a distal end, being slidably receivable in the second elongated flexible tube, the elongated catheter having an inflatable and deflatable cuff disposed about the distal end of the elongated catheter; and, an air passage defined in a wall of the first elongated flexible tube and terminating within the first inflatable and deflatable cuff.

2. The endotracheal apparatus as set forth in claim 1 wherein the distal ends of the first and second elongated tubes are angled relative to an axial direction.

3. The endotracheal apparatus as set forth in claim 1 wherein the first elongated tube includes an opening located between the distal end of the first elongated tube and the first inflatable and deflatable cuff, the opening allowing air to enter the first elongated tube.

4. The endotracheal apparatus as set forth in claim 1 wherein the second elongated tube has a diameter which is smaller than a diameter of the first elongated tube.

5. The endotracheal apparatus as set forth in claim 1 wherein the first and second elongated tubes are joined in contact.

6. The endotracheal apparatus as set forth in claim 1 further including a valve in fluid communication with the air passage for supplying air to and removing air from the first inflatable and deflatable cuff.

7. The endotracheal apparatus as set forth in claim 1 wherein the distal end of the elongated catheter is capable of extending beyond the distal end of the second elongated flexible tube and is directable by rotation into a selected bronchus.

8. The endotracheal apparatus as set forth in claim 1 further including a means to inflate and deflate the inflatable and deflatable cuff of the elongated catheter.

9. The endotracheal apparatus as set forth in claim 1 wherein the first and second elongated flexible tubes comprise a polyvinyl chloride material.

10. An endotracheal apparatus for insertion through the mouth and into the trachea of a patient for ventilating at least one lung comprising:

a first flexible tube having a sufficient length to extend from the mouth to a position near the carina of the trachea, the first flexible tube being adapted to communicate air;

a second flexible tube separate from the first flexible tube and having a length substantially equal to he length of the first flexible tube, the second flexible tube having a portion of an outer surface wall closely joined in a side-by-side relation with a portion of an outer surface wall of the first flexible tube, the second flexible tube being adapted to slidably receive an elongated instrument;

and, an elongated instrument having a bronchial blocking cuff sealed to a distal end of the elongated instrument, the elongated instrument being slidably received into the second flexible tube such that the distal end extends beyond a distal end of the second flexible tube and into the selected bronchus.

11. The endotracheal apparatus as set forth in claim 10 further including an inflatable and deflatable cuff sealed around both the first and second flexible tubes at a position to engage the trachea when the first and second flexible tubes are at the position near the carina and the inflatable and deflatable cuff is inflated; and, an air passage associated with one of the first and second flexible tubes, the air passage being adapted to communicate air to and from the inflatable and deflatable cuff.

12. The endotracheal apparatus as set forth in claim 11 further including a means to inflate and deflate the bronchial blocking cuff.

13. The endotracheal apparatus as set forth in claim 10 wherein the first and second flexible tubes are comprised of a polyvinyl chloride material.

14. The endotracheal apparatus as set forth in claim 10 wherein the first flexible tube has a diameter which is larger than a diameter of the second flexible tube.

15. The endotracheal apparatus as set forth in claim 10 further including a cuff inflator including a valve in fluid communication to the air passage to selectively inflate and deflate the inflatable and deflatable cuff.

16. A method of using an endotracheal apparatus for ventilating one lung and blocking the other lung of a patient comprising the steps of:

providing separate first and second flexible tubes closely joined in a side-by-side relation along their external walls, each of the first and second flexible tubes having a length sufficient to extend from the patient's mouth and into the patient's trachea, the second flexible tube being configured to receive an elongated catheter having a bronchial blocking cuff;

inserting the first and second flexible tubes through the mouth and into the trachea with a distal end of the first and second flexible tubes being at a position near the carina;

providing an elongated catheter having a bronchial blocking cuff disposed toward a distal end of the catheter;

inserting the distal end of the elongated catheter into the second flexible tube and maneuvering the bronchial blocking cuff into a bronchus; and, inflating the bronchial blocking cuff to occlude the bronchus.

17. The method of using an endotracheal apparatus as set forth in claim 16 further including securing the position of the first and second flexible tubes relative to the trachea.

18. The method of using an endotracheal apparatus as set forth in claim 16 further including while inserted in the second flexible tube, rotating the elongated catheter into a selected bronchus.

19. The endotracheal apparatus as set forth in claim 1 wherein the endobronchial blocker is rotatable in and removable from the second elongated flexible tube.

20. The endotracheal apparatus as set forth in claim 11 wherein the catheter is rotatable in and removable from the second flexible tube.

* * * * *